(12) United States Patent
Carson et al.

(10) Patent No.: US 9,089,421 B2
(45) Date of Patent: Jul. 28, 2015

(54) METHOD AND SYSTEM FOR PROVIDING AN INTRAOCULAR LENS HAVING AN IMPROVED DEPTH OF FIELD

(71) Applicant: NOVARTIS AG, Basel (CH)

(72) Inventors: Daniel Robert Carson, Fort Worth, TX (US); Myoung-Taek Choi, Arlington, TX (US); Shinwook Lee, Arlington, TX (US)

(73) Assignee: NOVARTIS AG, Basel (CH)

( * ) Notice: Subject to any disclaimer, the term of this patent is extended or adjusted under 35 U.S.C. 154(b) by 38 days.

(21) Appl. No.: 14/095,106

(22) Filed: Dec. 3, 2013

(65) Prior Publication Data

US 2014/0172088 A1    Jun. 19, 2014

Related U.S. Application Data

(60) Provisional application No. 61/738,571, filed on Dec. 18, 2012.

(51) Int. Cl.
*A61F 2/16*    (2006.01)

(52) U.S. Cl.
CPC ............. *A61F 2/1654* (2013.01); *A61F 2/1656* (2013.01)

(58) Field of Classification Search
CPC ............................. A61F 2/1654; A61F 2/1656
USPC ...................... 623/6.25, 6.26, 6.27, 6.28, 6.3; 351/159.11, 159.12
See application file for complete search history.

(56) References Cited

U.S. PATENT DOCUMENTS

| 2006/0098162 | A1 | 5/2006 | Bandhauer et al. |
| 2011/0098811 | A1 | 4/2011 | Hong et al. |
| 2011/0109874 | A1 | 5/2011 | Piers et al. |
| 2011/0149236 | A1 | 6/2011 | Weeber |
| 2012/0140166 | A1 | 6/2012 | Zhao |

OTHER PUBLICATIONS

PCT/US2013/72773; International Search Report, Feb. 4, 2014, 2 pgs.

*Primary Examiner* — David H Willse
*Assistant Examiner* — Javier Blanco
(74) *Attorney, Agent, or Firm* — Jason Finch

(57) ABSTRACT

A method and system provide an ophthalmic device. The ophthalmic device includes an ophthalmic lens having an anterior surface, a posterior surface, an optic axis and at least one diffractive grating pattern. The diffractive grating pattern(s) are disposed on at least one of the anterior surface and the posterior surface. The diffractive grating pattern(s) includes zones corresponding to distance ranges from the optic axis. Each of the zones has a plurality of echelettes having a radius of curvature corresponding to a focal length. The radius of curvature for each of at least a portion of the zones is different from the radius of curvature for another of the zones.

13 Claims, 4 Drawing Sheets

METHOD AND SYSTEM FOR PROVIDING AN INTRAOCULAR LENS HAVING AN IMPROVED DEPTH OF FIELD

This application claims the priority of U.S. Provisional Patent Application No. 61/738,571 filed on Dec. 18, 2012.

BACKGROUND

Intraocular lenses (IOLs) are implanted in patients' eyes either to replace a patient's lens or, in the case of a phakic IOL, to complement the patient's lens. For example, the IOL may be implanted in place of the patient's lens during cataract surgery. Alternatively, a phakic IOL may be implanted in a patient's eye to augment the optical power of the patient's own lens.

Some conventional IOLs are single focal length IOLs. Single focal length IOLs have a single focal length or single power. The focal length is generally fixed at a point relatively close to the patient, for example on the order of one meter from the patient. Objects at the focal length from the eye/IOL are in focus, while objects nearer or further away are out of focus. Although objects are in perfect focus only at the focal length, objects within the depth of field (within a particular distance of the focal length) still acceptably in focus for the patient to consider the objects in focus. However, patients may still require additional correction for objects that are closer or further away than the depth of field.

Some conventional IOLs may utilize diffraction to provide multiple focal lengths. Such conventional diffractive IOLs typically have two focal lengths-far and near. Diffractive IOLs utilize a diffraction grating formed on the anterior surface of the IOL. The diffractive grating typically takes the form of microscopic echelettes, or surface saw-tooth like facets, formed on the lens surface. The echelettes form a diffraction grating having a particular focal length. For example, some conventional bi-focal diffractive IOLs may break the lens into zone plates based upon distance from the optic axis. Each zone includes a single echelette having a radius of curvature proportional to the square root of the zone number, with odd zones having a step height for the echelette and even zones having half of the step height for the echelette. Such a conventional diffractive IOL may have two focal lengths. However, such a diffractive IOL may still have a limited depth of field around each focal length. As a result, a patient may still require additional correction for activities, such as reading, that may involve focusing objects outside of the depth of field for each focal length.

Accordingly, what is needed is a system and method for improving the depth of field in IOLs.

BRIEF SUMMARY OF THE INVENTION

A method and system provide an ophthalmic device and treat a patient using the ophthalmic device. The ophthalmic device includes an ophthalmic lens having an anterior surface, a posterior surface, an optic axis and at least one diffractive grating pattern. The diffractive grating pattern(s) are disposed on at least one of the anterior surface and the posterior surface. The diffractive grating pattern(s) includes zones corresponding to distance ranges from the optic axis. Each of the zones has a plurality of echelettes having a radius of curvature corresponding to a focal length. The radius of curvature for each of at least a portion of the zones is different from the radius of curvature for another of the zones.

DETAILED DESCRIPTION OF THE PREFERRED EMBODIMENTS

The exemplary embodiments relate to IOLs including diffractive gratings. The following description is presented to enable one of ordinary skill in the art to make and use the invention and is provided in the context of a patent application and its requirements. Various modifications to the exemplary embodiments and the generic principles and features described herein will be readily apparent. The exemplary embodiments are mainly described in terms of particular methods and systems provided in particular implementations. However, the methods and systems will operate effectively in other implementations. Phrases such as "exemplary embodiment", "one embodiment" and "another embodiment" may refer to the same or different embodiments as well as to multiple embodiments. The embodiments will be described with respect to systems and/or devices having certain components. However, the systems and/or devices may include more or less components than those shown, and variations in the arrangement and type of the components may be made without departing from the scope of the invention. The exemplary embodiments will also be described in the context of particular methods having certain steps. However, the method and system operate effectively for other methods having different and/or additional steps and steps in different orders that are not inconsistent with the exemplary embodiments. Thus, the present invention is not intended to be limited to the embodiments shown, but is to be accorded the widest scope consistent with the principles and features described herein.

A method and system described herein provide an ophthalmic device and treat a patient using the ophthalmic device. The ophthalmic device includes an ophthalmic lens having an anterior surface, a posterior surface, an optic axis and at least one diffractive grating pattern. The diffractive grating pattern(s) are disposed on at least one of the anterior surface and the posterior surface. The diffractive grating pattern(s) includes zones corresponding to distance ranges from the optic axis. Each of the zones has a plurality of echelettes having a radius of curvature corresponding to a focal length. The radius of curvature for each of at least a portion of the zones is different from the radius of curvature for another of the zones.

Figure 1:
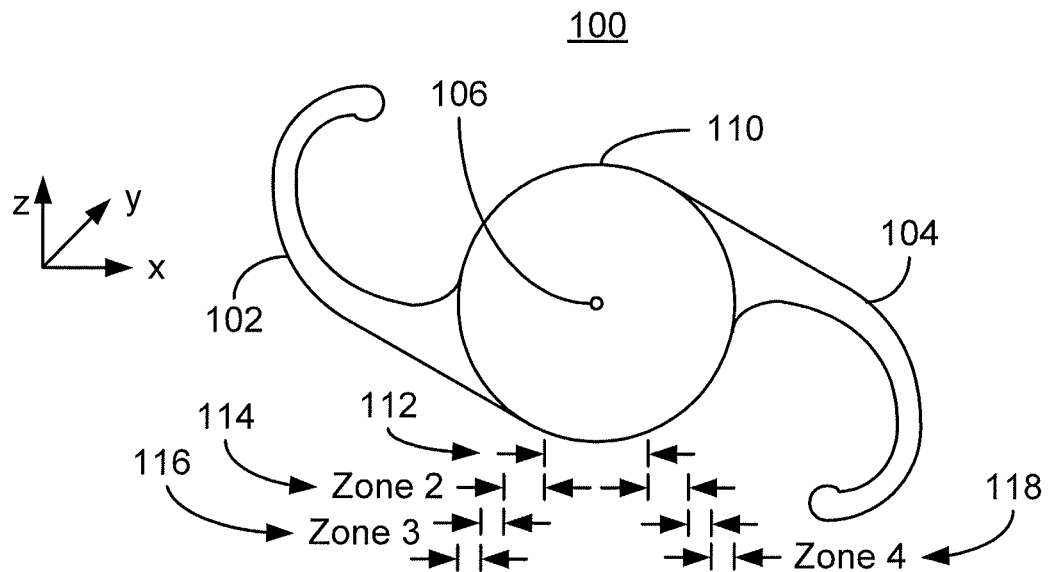
FIG. 1 depicts a plan view of an exemplary embodiment of an ophthalmic device.
Figure 2:
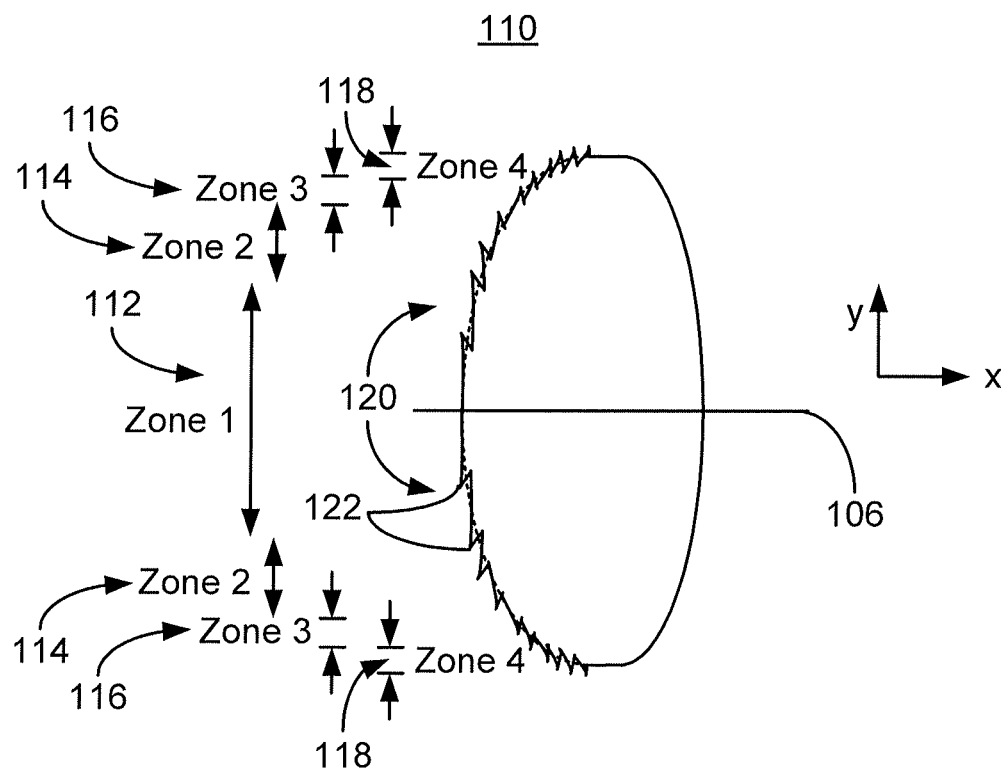
FIG. 2 depicts a side view of an exemplary embodiment of a lens of an ophthalmic device.

FIGS. 1-2 depict an exemplary embodiment of an ophthalmic device 100 that may be used as an IOL. FIG. 1 depicts a plan view of the ophthalmic device 100, while FIG. 2 depicts a side view of the ophthalmic lens 110. For clarity, FIGS. 1 and 2 are not to scale. The ophthalmic device 100 includes an ophthalmic lens 110 having an optic axis 106 as well as haptics 102 and 104. The ophthalmic lens may be made of a variety of optical materials including but not limited to one or more of silicone, a hydrogel, an acrylic and AcrySof®. Haptics 102 and 104 are used to hold the ophthalmic device 100 in place in a patient's eye (not explicitly shown). However, in other embodiments, other mechanism(s) might be used to retain the ophthalmic device in position in the eye. For clarity, the haptics are not depicted in FIGS. 2-7, discussed below. Although the ophthalmic lens 119 is depicted as having a circular cross section in the plan view of FIG. 1, in other embodiments, other shapes may be used.

The ophthalmic lens 110 is divided into zones based on a radial distance from the optic axis 106. In the embodiment shown, the ophthalmic lens 110 is divided into four zones: Zone 1 112, Zone 2 114, Zone 3 116 and Zone 4 118. Zone 1 112 is a circle corresponding to a zero radius (the optic axis) up to a first, smallest radius. Zone 2 114 is an annular ring from the first radius to a second radius that is larger than the first radius. Zone 3 116 is an annular ring from the second radius to a third radius that is larger than the second radius. Zone 4 118 is an annular ring from the third radius to a fourth radius that is larger than the third radius. In the embodiment shown, Zone 4 118 extends to the outer edge of the lens 110. However, in other embodiments, the zones need not extend to the outer edge of the lens 110.

The lens 110 also includes a diffraction grating 120 on the anterior surface of the lens 110. However, in other embodiments, the diffraction grating 120 may be on the posterior surface or diffraction gratings may exist on both the anterior and posterior surfaces of the lens 110. Further, if diffraction gratings 120 reside on both surface of the lens 110, there is no requirement that the diffraction gratings be the same. The diffraction grating 120 is shown with respect to a dotted line corresponding to a lens on which a diffraction grating is not provided. The diffraction grating 120 includes echelettes 122. For simplicity, only two echelettes 122 are labeled. In the embodiment shown, the diffraction grating 120 may have a diffraction order is +1, allowing the refractive portion of the lens 110 to be better incorporated with the diffraction grating 120.

The echelettes 122 of the diffraction grating 120 differ in the zones 112, 114, 116 and 118. More specifically, the radii of curvature of the surfaces of the echelettes 122 are zone dependent. Thus, the echelettes 122 in Zone 1 112 have a first radius of curvature, the echelettes 122 in Zone 2 114 have a second radius of curvature, the echelettes 122 in Zone 3 116 have a third radius of curvature and the echelettes 122 in Zone 4 118 have a fourth radius of curvature. At least some of the first, second, third and fourth radii of curvature differ from other radii of curvature. In the embodiment shown, the first radius of curvature of the echelettes 122 in Zone 1 112 is the largest, the second radius of curvature of the echelettes 122 in Zone 2 114 is the second largest, the third radius of curvature of the echelettes 122 in Zone 3 116 is the third largest and the fourth radius of curvature of the echelettes 122 in Zone 4 118 is the smallest. Thus, the radius of curvature monotonically decreases from lower zones to higher zones in FIG. 2. However, other dependencies are possible. For example, the radius of curvature may increase with increasing distance from the optic axis. Further, the radius of curvature for a zone 112, 114, 116 and/or 118 may also be configured to account for issues such as spherical aberration. Thus, in some embodiments, the radius of curvature does not monotonically increase or decrease from lower radius to higher radius zones. In most embodiments, however, the diffraction grating 120 is configured such that the focal length of the zone (as opposed to the radius of curvature of the zone) monotonically increases or monotonically decreases). In the embodiment shown, the step height for the echelettes 122 does not vary. Thus, the step height is the same for each of the zones 112, 114, 116 and 118. The local step height for the echelettes 122 in a particular zone corresponds to the optical efficiency for that zone. In some embodiments, therefore, the local step height is constant in order to provide a constant value of the optical efficiency for a particular wavelength of light. However, in other embodiments, the step height may vary.

In the embodiment shown, the local period of the diffraction grating 120 is given by $\Lambda = f\lambda/r$, where $\Lambda$ is the period, f is the focal length of the diffractive surface, r is the distance from the optic axis, and $\lambda$ is the wavelength of light. The focal length and the period, $\Lambda$, depend upon to the radius of curvature of the echelettes 122. As discussed above, the radii of curvature of the zones 112, 114, 116 and 118 differ. Thus, the focal length and grating period also differ in each of the zones 112, 114, 116 and 118.

The lens 110 may have an enhanced depth of field due to the varying radius of curvature of the echelettes in the zones 112, 114, 116, and 118. More specifically, the different radii of curvature for the echelettes in each of the zones 112, 114, 116 and 118 corresponds to different focal lengths for the zones 112, 114, 116 and 118. The diffraction grating 120 may thus be considered to have a blending of focal lengths for the zones 112, 114, 116 and 118, instead of a single focal length. Similarly, the depth of field for the diffraction grating 120 may also be a blending of the depths of field for the zones 112, 114, 116 and 118. The depth of field for the lens 110 may be extended by this blending of the depths of field. For example, suppose each zone has a depth of field around its own focal length and a particular focal length set by the radius of curvature of the echelettes in that zone. The depth of field for the lens 110 may include the depths of field of all of the zones 112, 114, 116 and 118 around the focal lengths of the zones 112, 114, 116 and 118. Thus, the depth of field for the lens 110 has been extended beyond that of a single zone 112, 114, 116, and 118. In some embodiments, the depth of field for the lens 110 including the diffraction grating 120 may be at least twice the depth of field of a single zone 112, 114, 116 or 118 of the diffraction grating. In some such embodiments, the depth of field for the lens 110 is at least thrice the depth of field of a single zone 112, 114, 116 or 118 of the diffraction grating. Thus, the depth of field for the lens 110 and, therefore, the ophthalmic device 100 may be increased by employing zones 112, 114, 116 and 118 having echelettes 122 with different radii of curvature.

Thus, the depth of field of the lens 110 may be enhanced. This increase in the depth of field may be achieved without changing the step height or otherwise adversely affecting the optical efficiency of the ophthalmic lens 110. The enhanced depth of field may be achieved without affecting the power of the lens 110. The diffraction grating 120 may be combined with refraction within the lens 110 to achieve the desired the lens power for the patient. Consequently, the ophthalmic device 100 and lens 110 may be better able to address vision issues in a patient.

Figure 3:
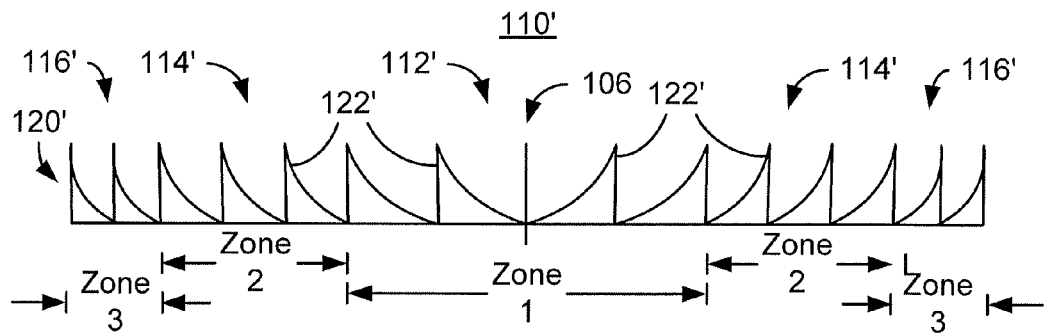
FIG. 3 depicts an exemplary embodiment of a diffractive grating for an exemplary embodiment of a portion of an ophthalmic device.
Figure 4:
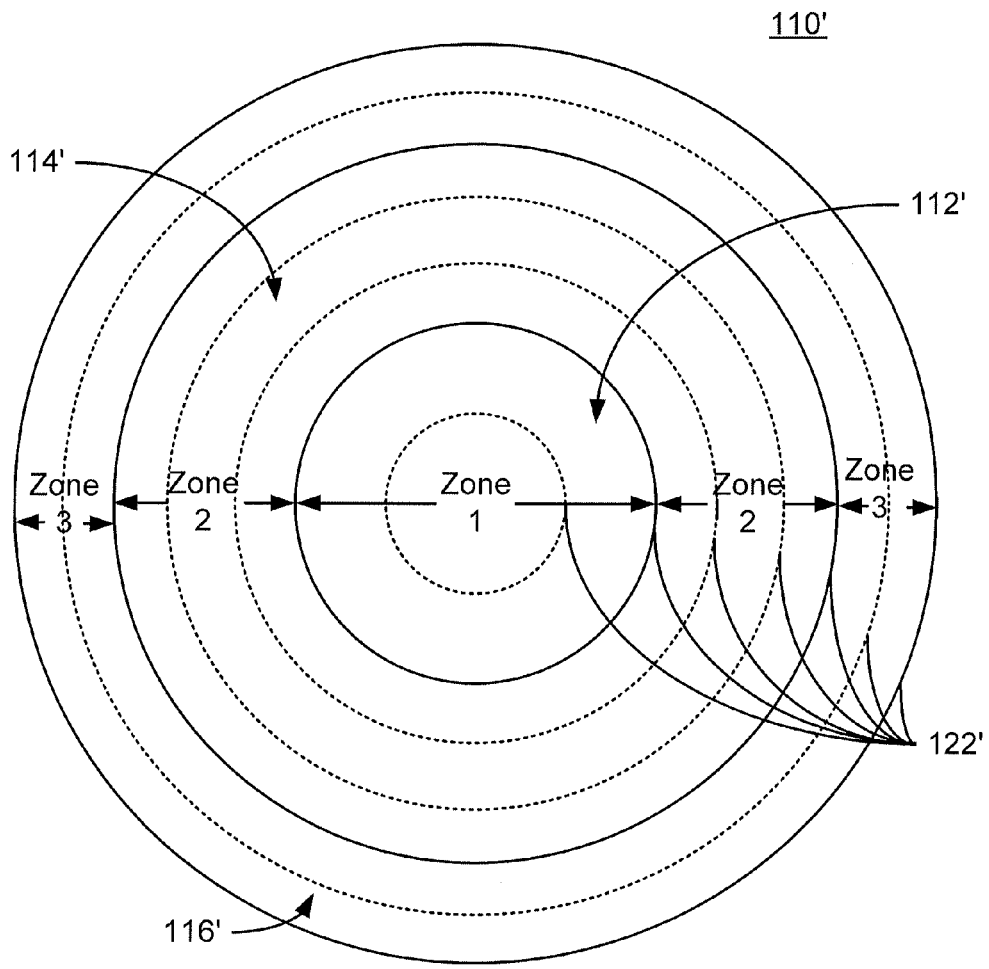
FIG. 4 depicts an exemplary embodiment of a lens for an exemplary embodiment of a portion of an ophthalmic device.

FIGS. 3 and 4 depict side and plan views of another exemplary embodiment of a lens 110'. FIGS. 3 and 4 are not to scale. The lens 110' is analogous to the lens 110 and thus may be incorporated into the ophthalmic device 100. The lens 110' includes an optic axis 106', zones 112', 114' and 116', as well as diffraction grating 120' including echelettes 122' (of which only four are labeled in FIG. 3) that are analogous to the optic axis 106, zones 112, 114 and 116 and diffraction grating 120 having echelettes 122, respectively. Thus, the structure and function of the components 106', 110', 112', 114', 116', 120' and 122' are analogous to that of the components 106, 110, 112, 114, 116, 120 and 122, respectively. For clarity, the side view of FIG. 3 depicts the lens 110' as though the surface on which the diffraction grating 120' resides is flat. However, the anterior and/or posterior surface on which the diffraction grating 120' resides is typically curved. Further, the tips of echelettes not residing at a zone boundary are shown as dotted lines in FIG. 4.

The echelettes 122' in the zones 112', 114' and 116' have three different radii of curvature. Zone 1 112' includes echelettes 122' having the largest radius of curvature. Zone 2 114' includes echelettes 122' having a middle radius of curvature. Zone 3 116' includes echelettes 122' having the smallest radius of curvature. Further, the radii of curvature may vary in another manner. Although only three zones 112', 114' and 116' are shown, another number may be used. As can be seen in FIG. 3, the echelettes 122' have a concave side having the radius of curvature that corresponds to the focal length of the zones 112', 114' and 116'. In the embodiment shown, the echelettes 122' in all three zones 112', 114' and 116' have different radii of curvature. However, in another embodiment, some of the zones may have the same radius of curvature. For example, the zone 112' may have the same radius of curvature as the zone 116'. In addition, the width of each zone 112', 114' and 116' in FIG. 3 is shown as different. However, in other embodiments, the zones 112', 114' and 116' may have the same width. Further, the echelettes 122' are depicted as ending at a zone boundary. However, in another embodiment, the echelettes 122' may not end at a boundary between zones 112', 114' and 116'.

The ophthalmic lens 110' shares the benefits of the lens 110 and ophthalmic device 100. The lens 110' may have an enhanced depth of field due to the varying radius of curvature of the echelettes 122' in the zones 112', 114', and 116'. This improvement in the depth of field may be achieved without adversely affecting the optical efficiency and power of the ophthalmic lens 110'. The diffraction grating 120' may be combined with refraction within the lens 110 to achieve the desired the lens power for the patient. Consequently, the ophthalmic device 100 and lens 110' may be better able to address vision issues in a patient.

Figure 5:
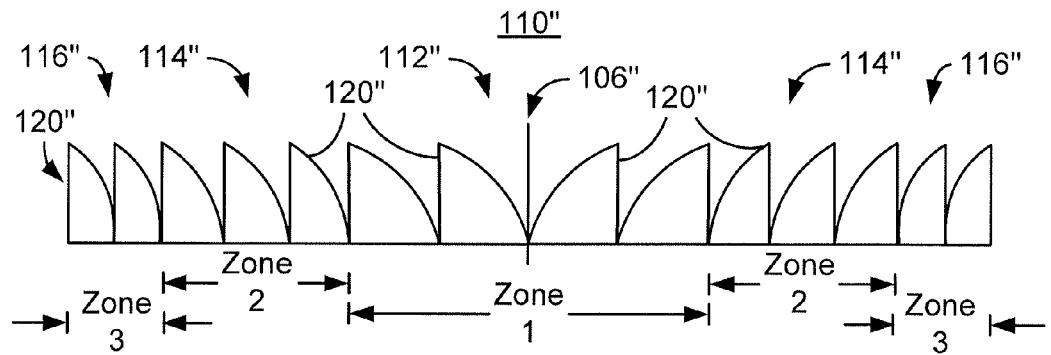
FIG. 5 depicts another exemplary embodiment of a diffractive grating for an exemplary embodiment of a portion of an ophthalmic device.
Figure 6:
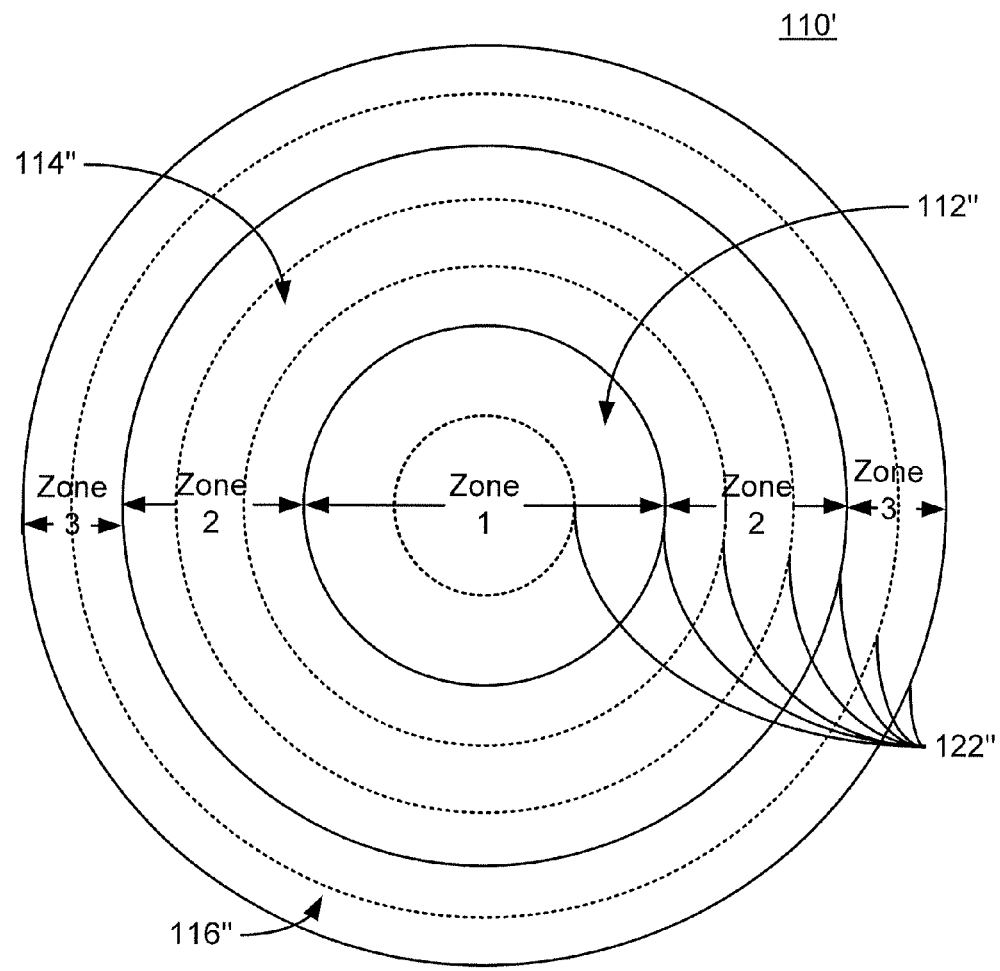
FIG. 6 depicts another exemplary embodiment of a lens for an exemplary embodiment of a portion of an ophthalmic device.

FIGS. 5 and 6 depict side and plan views of another exemplary embodiment of a lens 110". FIGS. 5 and 6 are not to scale. The lens 110" is analogous to the lenses 110 and 110'. The lens 110" thus may be incorporated into the ophthalmic device 100. The lens 110" includes an optic axis 106", zones 112", 114" and 116", as well as diffraction grating 120" including echelettes 122" (of which only four are labeled in FIG. 5) that are analogous to the optic axis 106/106', zones 112/112', 114/114' and 116/116' and diffraction grating 120/120' having echelettes 122/122', respectively. Thus, the structure and function of the components 106", 110", 112", 114", 116", 120" and 122" are analogous to that of the components 106/106', 110/110', 112/112', 114/114', 116/116', 120/120' and 122/122', respectively. For clarity, the side view of FIG. 5 depicts the lens 110" as though the surface on which the diffraction grating 120' resides is flat. However, the anterior and/or posterior surface on which the diffraction grating 120" resides is typically curved. Further, the tips of echelettes not residing at a zone boundary are shown as dotted lines in FIG. 4.

The echelettes 122" in the zones 112", 114" and 116" have three different radii of curvature. Zone 1 112" includes echelettes 122" having the largest radius of curvature. Zone 2 114" includes echelettes 122" having a middle radius of curvature. Zone 3 116" includes echelettes 122" having the smallest radius of curvature. Although only three zones 112", 114" and 116" are shown, another number may be used. Further, the radii of curvature may vary in another manner. As can be seen in FIG. 5, the echelettes 122" have a convex side having the radius of curvature that corresponds to the focal length of the zones 112", 114" and 116". In the embodiment shown, the echelettes 122' in all three zones 112', 114" and 116" have different radii of curvature. However, in another embodiment, some of the zones may have the same radius of curvature. For example, the zone 112" may have the same radius of curvature as the zone 116'". In addition, the width of each zone 112", 114" and 116" is shown as different. However, in other embodiments, the zones 112", 114" and 116" may have the same width. Further, the echelettes 122" are depicted as ending at a zone boundary. However, in another embodiment, the echelettes 122" may not end at a boundary between zones 112", 114" and 116".

The ophthalmic lens 110" shares the benefits of the lenses 110/110' and ophthalmic device 100. The lens 110" may have an enhanced depth of field due to the varying radius of curvature of the echelettes 122" in the zones 112", 114", and 116". This improvement in the depth of field may be achieved without adversely affecting the optical efficiency and power of the ophthalmic lens 110". The diffraction grating 120" may be combined with refraction within the lens 110" to achieve the desired the lens power for the patient. Consequently, the ophthalmic device 100 and lens 110" may be better able to address vision issues in a patient.

Figure 7:
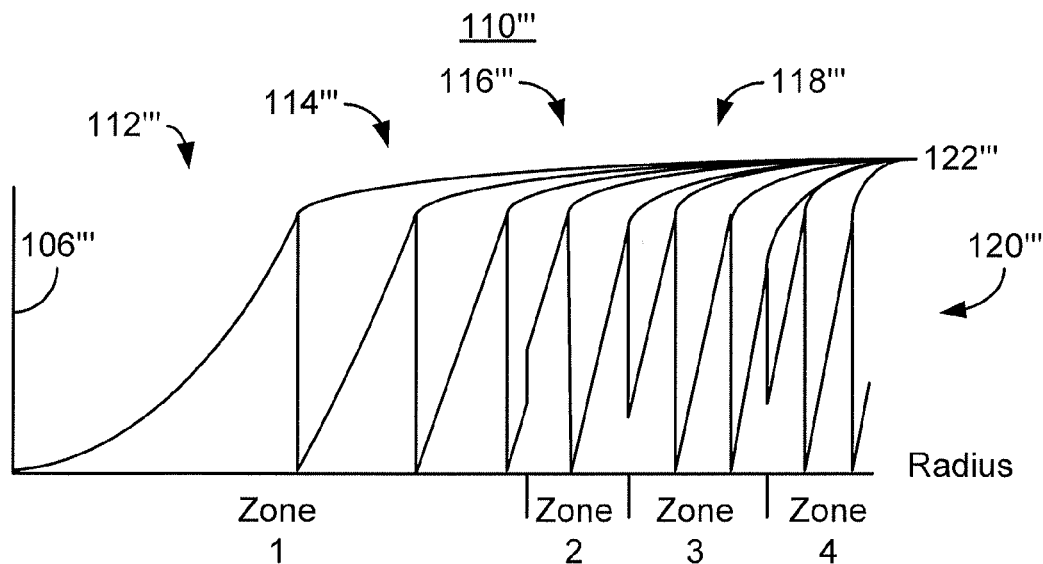
FIG. 7 depicts another exemplary embodiment of a lens for an exemplary embodiment of a portion of an ophthalmic device.

FIG. 7 depicts a side view of another exemplary embodiment of a lens 110'" having a diffraction grating 120'". FIG. 7 is not to scale. For clarity, the side view of FIG. 7 depicts the lens 110'" as though the surface on which the diffraction grating 120'" resides is flat. However, the anterior and/or posterior surface on which the diffraction grating 120'" resides is typically curved. The lens 110'" is analogous to the lenses 110, 110' and 110". The lens 110'" thus may be incorporated into the ophthalmic device 100. The lens 110'" includes an optic axis 106'", zones 112'", 114'", 116'" and 118'", as well as the diffraction grating 120'" including echelettes 122'" are analogous to the optic axis 106/106'/106", zones 112/112'/112", 114/114'/114", 116/116'/116" and 118 and diffraction grating 120/120'/120" having echelettes 122/122'/122", respectively. Thus, the structure and function of the components 106'", 110'", 112'", 114'", 116'", 120'" and 122'" are analogous to that of the components 106/106'/106", 110/110'/110", 112/112'/112", 114/114'/114", 116/116'/116", 118', 120/120'/120" and 122/122'/122", respectively. Although four zones 112'", 114'", 116'" and 118'" are shown, another number may be used.

The echelettes 122'" in the zones 112'", 114'", 116'" and 118'" have four different radii of curvature. Zone 1 112'" includes echelettes 122'" having the largest radius of curvature. Zone 2 114'" includes echelettes 122'" having a radius of curvature that is smaller than that of Zone 1 112'" and larger than that of Zone 3 116'". Zone 3 116'" includes echelettes 122'" having the smallest radius of curvature. However, the echelettes 122'" of Zone 4 118'" have a radius of curvature that is between that of the echelettes in Zone 1 112'" and Zone 2 114". The larger radius of curvature for the echelettes 122' in Zone 4 assists in accounting for other effects such as spherical aberrations. Further, the radii of curvature may vary in another manner. In addition, the step height of the echelettes 122'" is the same for all zones 112'", 114'", 116'" and 118'".

However, the echelettes 122''' may appear to have different facets and/or a smaller step height at or near boundaries between zones.

The ophthalmic lens 110''' shares the benefits of the lenses 110/110'/110'' and ophthalmic device 100. The lens 110''' may have an enhanced depth of field due to the varying radius of curvature of the echelettes 122''' in the zones 112''', 114''', 116''' and 118'''. This improvement in the depth of field may be achieved without adversely affecting the optical efficiency and power of the ophthalmic lens 110'''. The diffraction grating 120''' may be combined with refraction within the lens 110''' to achieve the desired the lens power for the patient. In addition, other aberrations may also be accounted for with the variation in the radius of curvature of the echelettes 122''. Consequently, the ophthalmic device 100 and lens 110''' may be better able to address vision issues in a patient.

The diffraction grating 120/120'/120''/120''' may be applied to the lens 110/110'/110''/110''' in a number of different methods. For example, the diffractive grating 120/120'/120''/120''' may be integral with the anterior and/or posterior surfaces of the lens 110/110'/110''/110'''. In some embodiments, the diffractive grating 120/120'/120''/120''' may be incorporated into the pattern of the mold that is used to form the lens. In another embodiment, the diffractive grating 120/120'/120''/120''' may be machined or etched into the anterior and/or posterior surfaces of the lens after the lens has been formed. In these embodiments, the material used to form both the main lens portion and the diffractive grating typically will be the same. Materials of used for ophthalmic lenses described herein include but are not limited to silicones, acrylics (including, e.g., AcrySof®), and hydrogels. In other embodiments, the diffractive grating 120/120'/120''/120''' may be fabricated separately from the lens surface and then fastened or coupled to the anterior and/or posterior surfaces of the lens after fabrication. In such embodiments, the diffractive grating may be fabricated of a different material than the main portion of the lens.

Figure 8:
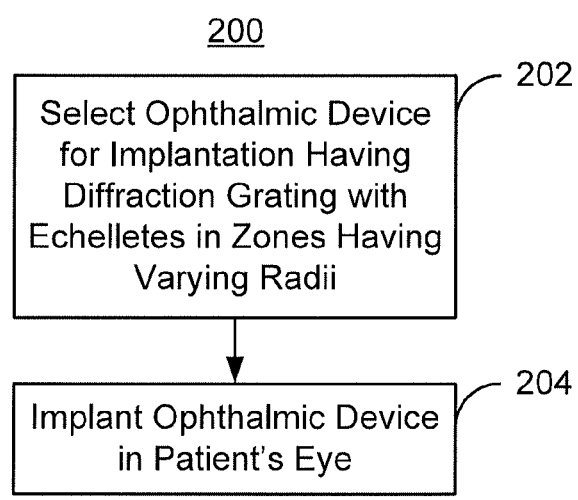
FIG. 8 is flow chart depicting an exemplary embodiment of a method for utilizing an ophthalmic device.

FIG. 8 is an exemplary embodiment of a method 200 for treating an ophthalmic condition in a patient. For simplicity, some steps may be omitted, interleaved, and/or combined. The method 200 is also described in the context of using the ophthalmic device 100 and ophthalmic lens 110. However, the method 200 may be used with one or more of ophthalmic lenses 110, 110', 110'', 110''' and/or an analogous ophthalmic device.

An ophthalmic device 100 for implantation in an eye of the patient is selected, via step 202. The ophthalmic device 100 includes an ophthalmic lens 110 having a diffraction grating 120. Thus, the ophthalmic device 100 including the ophthalmic lens 110, 110', 110'', or 110''' may be selected in step 202.

The ophthalmic device 100 is implanted in the patient's eye, via step 204. Step 204 may include replacing the patient's own lens with the ophthalmic device 100 or augmenting the patient's lens with the ophthalmic device. Treatment of the patient may then be completed. In some embodiments implantation in the patient's other eye of another analogous ophthalmic device may be carried out.

Using the method 200, the ophthalmic lens(s) 110, 110', 1110'', 110''' and/or ophthalmic lens may be used. Thus, the benefits of one or more of the ophthalmic lenses 110, 110', 110'', and/or 110''' may be achieved.

A method and system for providing an ophthalmic lens having a diffraction grating, an ophthalmic device including the lens and a method for using the ophthalmic device have been described. The method and systems have been described in accordance with the exemplary embodiments shown, and one of ordinary skill in the art will readily recognize that there could be variations to the embodiments, and any variations would be within the spirit and scope of the method and system. Accordingly, many modifications may be made by one of ordinary skill in the art without departing from the spirit and scope of the appended claims.

The invention claimed is:

1. An ophthalmic lens comprising:
   an anterior surface;
   a posterior surface;
   an optic axis; and
   at least one diffractive grating pattern disposed on at least one of the anterior surface and the posterior surface, the at least one diffractive grating pattern including a plurality of annular zones corresponding to a plurality of distance ranges from the optic axis, each of the plurality of zones having a plurality of echelettes having a radius of curvature corresponding to a focal length, the radius of curvature for each of the plurality of zones being different from the radius of curvature for another of the plurality of zones,
   wherein each of the plurality of echelettes has a step height, the step height for each of the plurality of zones being the same for all of the plurality of zones,
   wherein the radius of curvature for each of the plurality of zones changes monotonically with a zone distance from the optic axis,
   wherein the focal length corresponding to the radius of curvature for each of the plurality of zones changes monotonically with a zone distance from the optic axis,
   wherein each zone has a depth of field, wherein the depth of field for the ophthalmic lens is extended beyond that of a single zone by blending of the depths of field of the plurality of zones, and
   wherein a local period of the diffractive grating pattern is given by $\Lambda = f\lambda/r$, where $\Lambda$ is the period, $f$ is the focal length of the diffractive surface of a zone, $r$ is the distance from the optic axis, and $\lambda$ is the wavelength of light.

2. The ophthalmic lens of claim 1 wherein the radius of curvature for each of the plurality of zones is further configured to account for spherical aberrations of the ophthalmic lens.

3. The ophthalmic lens of claim 1 wherein the ophthalmic lens is made from at least one of silicone, a hydrogel, an acrylic and AcrySof®.

4. The ophthalmic lens of claim 1 wherein a zone of the plurality of zones has a first depth of field and wherein the ophthalmic lens has a second depth of field corresponding to the plurality of zones, the second depth of field being greater than the first depth of field.

5. The ophthalmic lens of claim 4 wherein the second depth of field is at least twice the first depth of field.

6. The ophthalmic lens of claim 4 wherein the second depth of field is at least three times the first depth of field.

7. An ophthalmic device comprising: an ophthalmic lens having an anterior surface, a posterior surface, an optic axis, and at least one diffraction pattern disposed on at least one of the anterior surface and the posterior surface, the at least one diffractive grating pattern including a plurality of annular zones corresponding to a plurality of distance ranges from the optic axis, each of the plurality of zones having a plurality of echelettes having a radius of curvature corresponding to a focal length, the radius of curvature for each of the plurality of zones being different from the radius of curvature for another of the plurality of zones; and a plurality of haptics coupled with the ophthalmic lens, wherein each of the plurality of echelettes has a step height, the step height for each of the plurality of zones being the same for all of the plurality of zones, wherein the radius of curvature for each of the plurality of zones changes monotonically with a zone distance from the optic axis, wherein the focal length corresponding to the radius of curvature for each of the plurality of zones changes monotonically with a zone distance from the optic axis, wherein each zone has a depth of field, wherein the depth of field for the ophthalmic lens is extended beyond that of a single zone by blending of the depths of field of the plurality of zones, and wherein a local period of the diffractive grating pattern is given by $\Lambda = f\lambda/r$, where $\Lambda$ is the period, f is the focal length of the diffractive surface of a zone, r is the distance from the optic axis, and $\lambda$ is the wavelength of light.

8. The ophthalmic lens of claim 7 wherein the radius of curvature for each of the plurality of zones is further configured to account for spherical aberrations of the ophthalmic lens.

9. The ophthalmic lens of claim 7 wherein the ophthalmic lens is made from at least one of silicone, a hydrogel, an acrylic and AcrySof®.

10. The ophthalmic lens of claim 7 wherein a zone of the plurality of zones has a first depth of field and wherein the ophthalmic lens has a second depth of field corresponding to the plurality of zones, the second depth of field being greater than the first depth of field.

11. The ophthalmic lens of claim 10 wherein the second depth of field is at least twice the first depth of field.

12. The ophthalmic lens of claim 10 wherein the second depth of field is at least three times the first depth of field.

13. A method for treating an ophthalmic condition in a patient comprising:

selecting an ophthalmic device for implantation in an eye of the patient, the ophthalmic device including an ophthalmic lens having an anterior surface, a posterior surface, an optic axis, and at least one diffraction pattern disposed on at least one of the anterior surface and the posterior surface, the at least one diffractive grating pattern including a plurality of annular zones corresponding to a plurality of distance ranges from the optic axis, each of the plurality of zones having a plurality of echelettes having a radius of curvature corresponding to a focal length, the radius of curvature for each of the plurality of zones being different from the radius of curvature for another of the plurality of zones; and implanting the ophthalmic device in the eye of the patient, wherein each of the plurality of echelettes has a step height, the step height for each of the plurality of zones being the same for all of the plurality of zones, wherein the radius of curvature for each of the plurality of zones changes monotonically with a zone distance from the optic axis, wherein the focal length corresponding to the radius of curvature for each of the plurality of zones changes monotonically with a zone distance from the optic axis, wherein each zone has a depth of field, wherein the depth of field for the ophthalmic lens is extended beyond that of a single zone by blending of the depths of field of the plurality of zones, and wherein a local period of the diffractive grating pattern is given by $\Lambda = f\lambda/r$, where $\Lambda$ is the period, f is the focal length of the diffractive surface of a zone, r is the distance from the optic axis, and $\lambda$ is the wavelength of light.

* * * * *